(12) United States Patent
Joensuu et al.

(10) Patent No.: US 10,266,562 B2
(45) Date of Patent: Apr. 23, 2019

(54) CONCENTRATION AND PURIFICATION OF HYDROPHOBINS AND ANTIBODIES WITH A PHASE SEPARATION METHOD

(71) Applicant: Teknologian tutkimuskeskus VTT Oy, Espoo (FI)

(72) Inventors: Jussi Joensuu, Espoo (FI); Markus Linder, Espoo (FI); Eero Mustalahti, Espoo (FI); Katri Kurppa, Espoo (FI)

(73) Assignee: Teknologian tutkimuskeskus VTT Oy, Espoo (FI)

( * ) Notice: Subject to any disclaimer, the term of this patent is extended or adjusted under 35 U.S.C. 154(b) by 519 days.

(21) Appl. No.: 14/902,851

(22) PCT Filed: Jul. 1, 2014

(86) PCT No.: PCT/FI2014/050545
§ 371 (c)(1),
(2) Date: Jan. 5, 2016

(87) PCT Pub. No.: WO2015/001187
PCT Pub. Date: Jan. 8, 2015

(65) Prior Publication Data
US 2016/0159854 A1     Jun. 9, 2016

(30) Foreign Application Priority Data

Jul. 5, 2013   (FI) .................................. 20135750

(51) Int. Cl.
| C07K 1/14 | (2006.01) |
| C07K 14/31 | (2006.01) |
| B01D 11/04 | (2006.01) |
| C07K 14/37 | (2006.01) |

(52) U.S. Cl.
CPC .......... *C07K 1/145* (2013.01); *B01D 11/0492* (2013.01); *C07K 14/31* (2013.01); *C07K 14/37* (2013.01); *C07K 2319/01* (2013.01)

(58) Field of Classification Search
None
See application file for complete search history.

(56) References Cited

U.S. PATENT DOCUMENTS

| 5,510,247 A | 4/1996 | Komives |
| 7,335,492 B2 * | 2/2008 | Penttila ................... C07K 1/14 |
| | | 435/41 |

FOREIGN PATENT DOCUMENTS

| EP | 2196470 A1 | 6/2010 |
| MX | 200901360 A | 7/2011 |
| WO | WO0058342 A1 | 10/2000 |

OTHER PUBLICATIONS

Linder et al: Efficient purification of recombinant proteins using hydrophobins as tags in surfactant-based two-phase systems. 2004.
Vazquez-Villegas P et al: Low-abundant protein extraction from complex protein sample using a novel continuous aqueous two-phase systems device. 2013.
Hu R. et al: Rapid highly efficient extraction and purification of membrane proteins using a microfluidic continuous-flow based aqueous two-phase system. JoC, 2011, vol. 1218.
Mao L.N. et al: Downstream antibody purification using aqueous two-phase extraction. Bp, 2010, vol. 26, No. 6.

* cited by examiner

*Primary Examiner* — Daniel E Kolker
*Assistant Examiner* — James L Rogers
(74) *Attorney, Agent, or Firm* — Seppo Laine Oy

(57) ABSTRACT

The present invention relates to a purification and concentration method for proteins and antibodies. Particularly the present invention relates to a continuous surfactant based phase separation method for recovering hydrophobin fusion proteins, and for recovering target molecules, such as antibodies, directly from a liquid by using phase separation and hydrophobin-Protein A fusion technologies.

13 Claims, 1 Drawing Sheet

CONCENTRATION AND PURIFICATION OF HYDROPHOBINS AND ANTIBODIES WITH A PHASE SEPARATION METHOD

BACKGROUND OF THE INVENTION

Field of the Invention

The present invention relates to a method for purifying proteins with a phase separation method, by using hydrophobin technology. In particular, the present invention relates to a continuous purification method for hydrophobin fusion protein(s), which results various benefits to different protein industries. In addition, the present invention relates to a method for purifying antibodies directly from a solution with means of a hydrophobin-Protein A fusion and a continuous phase separation technology.

Description of Related Art

Purification of proteins is generally performed by chromatography. Usually gel-chromatographic methods are used, based on ion-exchange, hydrophobic interaction, affinity chromatography and molecular sieving. Methods like electrophoresis and crystallization are also traditional. These methods are well known in the art and suitable for proteins of fairly high market value. In case of bulk protein production these methods, however, are too expensive in order to keep the final product on a compatible price level. Due to similar properties of these proteins several purification steps are usually needed to separate the proteins from each other. This often causes low final yields and therefore a high loss of product.

An example of useful proteins facing problems in purification in a cost-effective way are the commonly used industrial enzymes used as biocatalysts, glycosyl hydrolases, proteases and lipases produced by fungi and bacteria. These are used in e.g. laundry, textile, paper and pulp, food and feed industry. The fact that microbes produce many different enzymes during their growth and the fact that some of these may be undesired in certain applications leads to a need to enrich the active component(s). This enrichment can be performed by choosing appropriate growth conditions, by genetic engineering and/or by downstream processing (e.g. purification of the active component(s)).

Liquid-liquid extraction in an aqueous two-phase system (ATPS) can offer a powerful technique for isolation and purification of proteins. The separation of macromolecules and particles by means of liquid-liquid extraction is well known (Albertsson, 1986, Walter et al., 1985 and Kula, 1990). Mainly polyethylene glycol (PEG)-salt, PEG-dextran and PEG-starch systems have been in use. More recently detergents and detergents with reversed solubility were discovered as suitable methods for separation of macromolecules, and especially for the separation of proteins.

In aqueous two phase systems the desired target e.g. a protein should partition selectively into one phase while the other substances should partition into the other phase. In PEG/salt and PEG/dextran and similar systems there are several driving forces for a substance to phase-partition, for example, van der Waals or electrostatic forces and conformation or ligand interactions (Albertsson, 1986). The factors leading to separation in detergent-based aqueous two-phase systems are suggested to be primarily hydrophobic interactions (Terstappen et al., 1993). Even though a lot of research has been carried out in the field ATPS, none of the designed models provide a holistic view of the phase behavior leaving the predictability of protein separation low (Johansson et al., 1998).

In ATPS the partitioning coefficient K is defined as the concentration (activity in case of an enzyme) of the target in the top phase divided by the concentration (enzyme:activity) of the target protein in the bottom phase. Partitioning coefficients in ATPS systems are usually in the range from less than 1 up to less than 100 (Terstappen et al., 1992 and Terstappen et al., 1993).

$$K = \frac{c_{i,T}}{c_{i,B}}$$

Yield Y is defined as the amount of target in the top phase divided by the sum of the amount of target in top and bottom. This leads to the following equation:

$$Y_T = \frac{1}{1 + \left[\frac{V_B}{V_T} \cdot \frac{1}{K}\right]}$$

If the desired substance is directed to the heavier phase (as can be the case when using for example Triton X-114 as the detergent) the yield is defined by the following equation:

$$Y_B = \frac{1}{1 + \left[\frac{V_T}{V_B} \cdot K\right]}$$

The volume ratio of the two coexisting phases is defined by the volumes of the lighter over the heavier phase, respectively:

$$R = \frac{V_T}{V_B}$$

Extraction systems based on non-ionic surfactants have been described as an alternative to standard polymer-polymer or polymer-salt systems. Phase forming surfactants are e.g. polyoxyethylene type non-ionic detergents. The basis of this type of aqueous two-phase system is a temperature-dependent reversible hydration of the polar ethyleneoxide head groups. The temperature at which the phase-separation occurs is referred to as the cloud-point temperature (cloud-point extraction). This kind of aqueous two-phase system is especially suited for the extraction of amphiphilic biomolecules. The potential of this type of two-phase system for separating membrane bound proteins from cytosolic and peripheral membrane proteins was first demonstrated by Bordier (1981). In this research a non-ionic temperature sensitive detergent, Triton X-114, was used for separating integral membrane proteins from hydrophilic proteins into a surfactant phase, and the gel electrophoresis results showed that the extraction was successful.

Hydrophobins are bipolar and small proteins, consisting of about 100 to 150 amino acids, of which 8 are cysteine residues. They are expressed by filamentous fungi to help the organism, adapt better to the surrounding environment. The hydrophobins have an affinity for interfaces and are thus known for their ability to form coatings on hydrophobic surfaces. Hydrophobins are usually divided into two classes (class I and class II) based on their hydropathy profiles. Prior art has proposed various uses and applications for hydrophobins and derivatives thereof, such as stabilizing liquid phases (US 20090282729 A1), use as emulsifiers, thickeners and surface-active substances (WO 96/41882), treating materials in cosmetic applications (WO 03/53383) and coating various surfaces (EP 1252516 B1 and WO 03/10331).

Herein the main focus is in protein separation methods that use hydrophobin technology. Relating more closely to the subject matter of the present invention, it has been previously demonstrated, that hydrophobins and hydrophobin fusion proteins can be purified and concentrated with a surfactant based batch phase separation method (U.S. Pat. No. 7,060,669 B1 and U.S. Pat. No. 7,335,492 B2). These US-patents describe isolation and purification of proteins in aqueous two-phase systems (ATPS). Particularly these inventions provide processes and micro-organisms for partitioning of molecules of interest in ATPS by fusing said molecules to target proteins, which have the ability of carrying said molecule into one of the phases.

In U.S. Pat. No. 7,060,669 the targeting protein, such as a hydrophobin-like protein or parts of it, is fused to the product molecule or the component to be separated. First, phase forming materials and eventually possibly also additional salts are added to an aqueous solution containing the fusion molecule or component. The added agents are mixed to facilitate their solubilization. As soon as they are solubilized the two phases are formed either by gravity settling or centrifugation. In the separation the targeting protein drives the product to for instance the detergent-rich phase which could either be the top or the bottom phase. The method is not only useful for purification of products of interest but also for keeping the product or the component of interest, such as a biocatalyst, in a particular phase which enables certain useful biotechnical reactions.

It is however challenging to perform this kind of phase separation in larger scale, because usually if the volumes are high, phase separation is slow. Another problem is the instability of a target protein in required extraction conditions, which causes limitations for utilizing such method. Developing a continuous protein phase separation method would facilitate the handling of high volumes and improve the yields, especially for sensitive target molecules. In a cost-effective protein production process, where production fermenters are working continuously, also the downstream process, herein purification method would preferably be continuous.

Antibodies form an important molecular group especially for pharmaceutical industry and diagnostic industry. They are also the most significant biological medicinal molecular group now and at least in the near future. As the current situation is in most protein industries, also in antibody-relating processes most of the production costs come from purification steps. Prior purification technology is based on sepharose beads, to which antibody-binding proteins have been inserted. For example Protein A column chromatography is commonly used in the pharmaceutical industry for antibody purification. However, it is expensive to produce said beads and their lifetime is limited mostly because of impurities, which cause fouling. Sepharose-based purification and separation of biomolecules are carried out in batch-reactions, which also limits the scalability of these processes.

McLean et al. (2012) have recently studied the production of therapeutic monoclonal antibodies (MA) using genetically modified plants. Researchers used Protein A-oleosin oilbodies (Protein A-OB), expressed in transgenic safflower seeds for capturing MAs, from plants. A purification process for recovering Trastuzumab-antibody was developed, wherein Protein A-OB is mixed with crude extracts from plants engineered to express therapeutic antibodies, the Protein A-OB captures the antibody in the oilbody phase thus leaving the impurities in the aqueous phase. Remaining impurities and purified antibody are finally recovered by the means of centrifugation. Thus, this process also uses phase separation method, but it is aimed at overcoming fouling problems encountered in traditional chromatography technology. In addition, the process is not continuous and uses a different protein approach (oleosin) for recovering therapeutic antibodies.

A continuous purification and concentration method for proteins and antibodies achieved by using phase separation and hydrophobin fusion technologies will raise interest among industries that depend on protein production, such as enzyme, pharmaceutical, food & feed and chemical industries.

SUMMARY OF THE INVENTION

The aim of the invention is to provide a protein concentration and purification method for hydrophobin(s) or hydrophobin-like protein(s) by using phase separation technology.

In particular, an aim of the present invention is to provide a method for concentrating and purifying hydrophobin fusions in a continuous aqueous two-phase system (ATPS).

Another aim of the invention is to provide a purification method for target molecules (such as antibodies, small biomolecules as well as organic and inorganic nanoparticles). Antibody purification method utilizes in particular hydrophobin-Protein A (or other antibody-binding protein) fusion and phase separation technology.

These and other objects are achieved by the present invention as described and claimed herein.

More specifically, the method for purifying hydrophobin fusion proteins in a continuous phase separation system is characterized by what is stated in claim 1.

Furthermore, the method for purifying antibodies by continuous phase separation and hydrophobin technology is characterized by what is stated in claim 6, and the use of said methods is characterized by what is stated in claim 14.

One particular advantage of the present invention is that the separation and purification method of the desired hydrophobin, hydrophobin fusion protein, or antibodies can be carried out continuously. As a result, unnecessary delays in the phase separation process or increased impurity levels in the separated phases can be avoided, as compared to conventional batch separation methods.

In addition, scale-up of the methods presented in this invention is facile and straightforward.

Next, the invention will be described more closely with references to the attached drawings and a detailed description.

DETAILED DESCRIPTION OF THE PREFERRED EMBODIMENTS OF THE INVENTION

Figure 1:
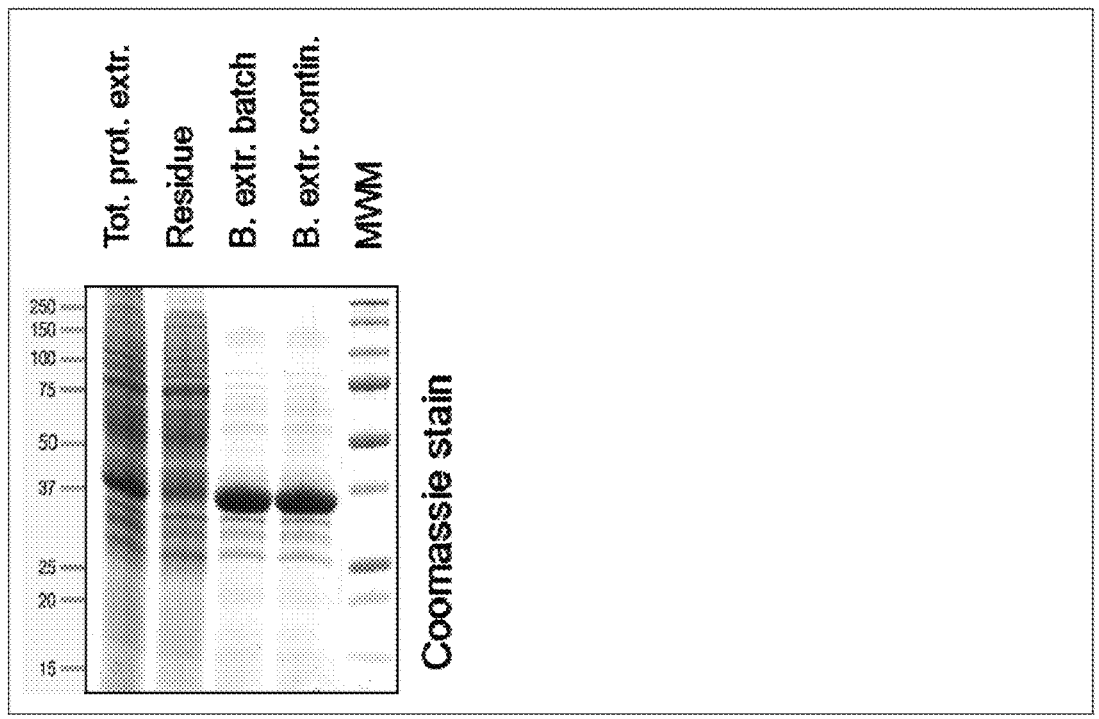
FIG. 1 describes the results of the continuous ATPS (aqueous two phase separation) process via SDS-PAGE analysis, showing that the fusion protein can be purified to similar level as observed with batch ATPS.
Figure 2:
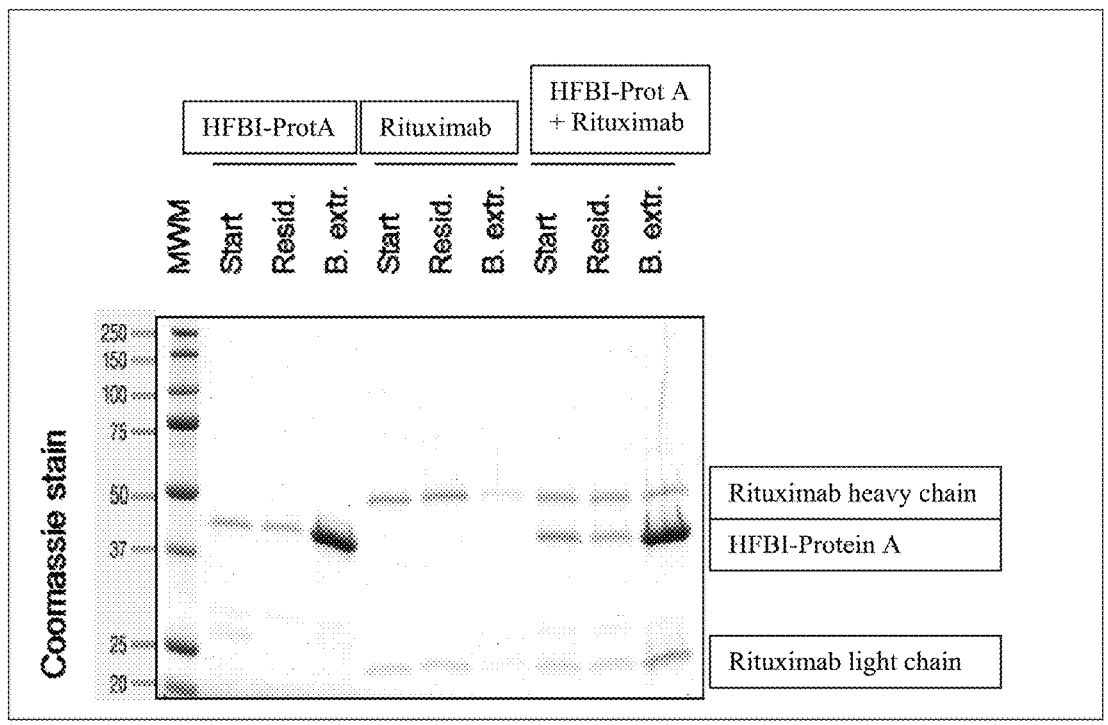
FIG. 2 is an SDS-PAGE analysis of ATPS samples, which show that a HFBI-Protein A fusion protein can capture Rituximab-antibody in the ATPS process.

In phase extraction methods many factors affect to the separation of surfactant and aqueous phases, such as extraction temperature, time, volume, pH, as well as ion and surfactant concentrations. It is also difficult to predict how target protein behaves when extraction conditions and scale changes.

In the present phase separation method a surfactant is mixed to the protein liquid, which contains at least one hydrophobin or hydrophobin-like protein, to form an extraction solution. Mixing is continued at least until a thorough contact has been achieved between the surfactant and the hydrophobin or hydrophobin-like protein, or a fusion protein thereof. The mixture is then transferred to a separation vessel and phases are allowed to separate. After initial phase separation, mixed extraction solution is continuously added to the separation vessel. Simultaneously, a separated stream of the surfactant phase and a separated stream of the aqueous phase are continuously removed from the extraction solution.

Preferably, the thoroughly mixed extraction solution i.e. extractable solution is pumped into a separation vessel with a first flow speed, in which vessel a surfactant phase and an aqueous phase is allowed to separate i.e. phase equilibrium is reached in the separation vessel. A part of the separated surfactant phase and a part of the aqueous phase are continuously removed from the separation vessel with a second flow speed, which keeps the volumes of the phase statues in the separation vessel unchangeable. The same process can be applied in back extraction process, wherein a suitable organic solvent removes the surfactant from the surfactant phase, thus leaving a concentrated and purified hydrophobin (s) or hydrophobin-like protein(s).

In a preferred embodiment the hydrophobin or the hydrophobin-like protein, having the capability to carry the molecule or particle of interest to the desired phase in ATPS, has been fused with molecules and particles that ought to be separated. Methods for fusing molecules with targeting proteins, e.g. hydrophobin, can be found for example from U.S. Pat. No. 7,060,669 B1. These methods include, mentioning few, genetic tagging, chemical binding and glueing, which are generally known in the art. These methods thus result a hydrophobin fusion molecule.

In another preferred embodiment the first flow speed and the second flow speed are adjusted together in a way that the volume of the surfactant phase and the aqueous phase keeps constant in the separation vessel. Preferably this means that the first flow from the mixing step to the separation vessel and the second flow removing separated phases from the separation vessel are equal or close to equal during the separation cycle.

"One separation cycle" means herein that at least an essential part of molecules to be separated and purified go through all above mentioned steps. In other words this means a process between time points $t_0$ and $t_1$, $t_0$ meaning a starting point when molecules of interest are added to the mixing step and $t_1$ meaning a point when said molecules are removed from the separation vessel (preferably as a part of the surfactant phase).

The second flow speed means a speed of the total (i.e. combined) removal flow of the separated phases from the separation vessel. Preferably, the separated surfactant phase and the separated aqueous phase are removed with a same (single) flow speed, but said speeds can also be different.

Herein the words "surfactant" and "detergent" are both used, thus meaning an organic substance or solution that reduces the surface tension of a liquid and is able to bind the target protein, or a derivative thereof, to itself from the aqueous extract that usually has a rather low protein concentration. Surfactant or detergent can be lighter or heavier than water. Non-ionic surfactants are preferred, because they are gentle towards target proteins and cause minimum protein degradation. Other useful features for good surfactants are that they work in the required (low) extraction temperature and contain as little as possible technical additives/impurities. Further, in a cost-effective process low surfactant amounts are favored and if possible, they should also be recycled back to the process.

Some of the suitable surfactants that can be used in the present invention are presented in Table 1.

TABLE 1

Preferred commercial surfactants

| Supplier | Product name | Chemical name/description |
|---|---|---|
| Celego (Seppic Pharma) | Montanox 80 VG DF<br>Montanox 81<br>Montanox 20 DF<br>Montanox 40 DF<br>Montanox 60 DF | Ethoxylated Sorbitan Ester |
| DOW Chemicals (Sigma-Aldrich) | Triton CF 32 | Polyoxyethylene polyoxypropylene tert-C12-13-alkyl amine |
| | Triton X-114 | Polyethylene glycol tert-octyphenyl ether |
| | Tergitol MinFoam 1x | Poly(ethylene glycol-co-propylene glycol) monobutyl ether) |
| BASF | Lutensol TO89 (90% liquid TO10)<br>Lutensol TO109 (90% liquid TO10)<br>Lutensol XL40<br>Lutensol XL50<br>Lutensol XL60<br>Lutensol XL70<br>Lutensol XL80<br>Lutensol AO 7<br>Lutensol AO 89 (90% liquid AO8) | Ethoxylated alkyl polyethylene glycol ether (based on C10-Guerbet alcohol) |
| Croda | Synperonic PE/L44<br>Synperonic PE/L62<br>Synperonic PE/L64 | Ethoxylated polypropylene oxide |
| | Synperonic LF28<br>Synperonic LF29<br>Synperonic LF30 | Ethylene oxide/propylene oxide copolymer (based on C13/C15 alcohol) |
| | Brij L4 | Ethoxylated natural fatty acid (based on lauryl alcohol) |
| | Brij LT3<br>Brij LT4 | Alkyl polyglycol ether |
| | Brij C2<br>Brij C10 | Ethoxylated natural fatty alcohol (based on cetyl alcohol) |
| | Brij CS6 | Alkyl polyglycol ether |
| Akzo Nobel | Berol 266<br>Ethylan1003 | Ethoxylated alcohol |

Surfactants that are used in the present invention perform ideally but not necessary in temperatures below 50° C. For example temperatures from 20° C. to 60° C. can be used, in order for the separation to be sensitive enough towards target molecules.

Separation efficiency, i.e. partitioning coefficients can be improved by adding salt(s) or other additives to the solution to be extracted. For example salts such as sodium chloride, NaCl, or ammonium sulfate, $(NH_4)_2SO_4$, can be used in proper amounts. Addition of salt(s) can make the phase separation significantly quicker and prevents emulsification.

Another factor relating to the separation efficiency is the amount of the surfactant that is mixed with separation solutions. Surfactant concentration should be selected so that the partitioning coefficient and target recovery rate remain as high as possible. An example of a suitable surfactant concentration is between 1-20% (weight/volume) of the reaction volume. In one particular embodiment concentrations between 1-10% (weight/volume) of the reaction volume are used.

In back-extraction method C1-C6 alcohols or block co-polymers are preferred, with isobutanol being particularly preferred, because of its capability to intake surfactant(s) reasonably well. Back extraction can also be performed continuously including a mixing step between the separations.

One advantage of the present invention is that the separation and purification method of the desired hydrophobin, or hydrophobin-like molecule, or hydrophobin fusion molecule can be carried out continuously. In an ideal protein production process this would mean no delays between production and downstream processing. In reality delays exist, but a continuous down streaming is more efficient than batch separation/purification methods. Further, it was discovered that changing the batch process into a continuous process causes essentially no delays in the phase separation and essentially no increase in impurity levels in the separated phases.

Particularly, the continuous process of the present invention can be scaled up, compared to the batch process, for example by adding plurality of parallel separation vessels (2). By using relatively small separation vessels, which are preferably heat adjustable, the phase separation speed can be maintained or even improved when handling large extraction volumes. Thus, no large reactors are needed, even in an up-scaled process, which makes the process more cost-effective and easier to adjust.

It has been found out, that hydrophobin related phase separation technology can also be utilized in purification of antibodies, because antibody-binding protein(s) can merge or fuse into hydrophobin(s). Herein primary purification is preferably based on Protein A, which has been isolated from *Staphylococcus*, in particular from *Staphylococcus aureus*. Protein A binds to the conserved Fc-part of the heavy chain of the antibody. Aqueous solution that contains antibodies is mixed with hydrophobin-Protein A-fusion protein(s) and with phase separation inducing surfactant. Antibodies that bind to Protein A are thus transferred from the aqueous phase into the surfactant phase. The present method for antibody separation is preferably carried out continuously by following similar steps as described previously in the separation/purification method for hydrophobin fusion(s).

In a preferred embodiment antibodies are released from Protein A by using a suitable low pH-buffer, such as glycine-HCl buffer (pH e.g. from 1.5 to 3.0, such as 2.2), after which the aqueous phase containing the antibodies is collected. Remaining surfactant phase with hydrophobin and Protein A can be recycled back to the separation step.

Protein A is a cell wall protein, originally found from *Staphylococcus aureus*, having an average molecular weight of 42 000 Da. Because of its features, Protein A has the ability to bind immunoglobulins and because its capacity to bind antibodies with high affinity in general, it is widely used in biochemical industries. Therefore it is also a useful tool herein.

The present invention is not, however, limited to Protein A, which can for example be changed to Protein G or Protein S from the same origin, *Staphylococcus aureus*. These have been found to have similar binding characteristics.

It is also understood by a skilled reader that "hydrophobin" means generally all hydrophobins or hydrophobin-like molecules, for example HFBI, HFBII, Sc3p, cerato-ulmin and cryparin, although the experiments that are described in the examples have been carried out with HFBI.

The present invention is illustrated by the following non-limiting examples. It should be understood, however, that the embodiments given in the description above and in the examples are for illustrative purposes only, and that various changes and modifications are possible within the scope of the claims.

Example 1. A Process for Purification of Hydrophobin Fusion Proteins with Continuous Aqueous Two Phase Separation (ATPS)

Surfactant (Triton X-114) was mixed with total protein extract, containing the hydrophobin fusion protein. Herein GFP-HFBI was used, because of easy visualization under UV-light. The mixture was then transferred to a separation vessel while simultaneously removing the separated surfactant phase containing the hydrophobin fusion. Samples were analyzed with fluorometry and SDS-PAGE. Results show that the continuous ATPS process can purify and concentrate the fusion protein to similar level as observed with batch ATPS.

Example 2. Aqueous Two Phase Separation (ATPS)-Based Capture of Antibodies from Solution with Hydrophobin-Protein A Fusions HFBI Protein A was added to a media, containing antibodies, and phase separation was launched by adding a polyoxyethylene surfactant (Agrimul NRE). Protein A binds to an antibody heavy chain constant region. Thus, HFBI-Protein A-antibody complex was formed and it concentrated to a surfactant phase.

Thus, while there have been shown and described and pointed out fundamental novel features of the invention as applied to a preferred embodiment thereof, it will be understood that various omissions and substitutions and changes in the form and details of the method and device may be made by those skilled in the art without departing from the spirit of the invention. For example, it is expressly intended that all combinations of those elements and/or method steps which perform substantially the same results are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

CITATION LIST—PATENT LITERATURE

1. US 20090282729 A1
2. WO 96/41882
3. WO 03/53383
4. EP 1252516 B1
5. WO 03/10331
6. U.S. Pat. No. 7,060,669 B1
7. U.S. Pat. No. 7,335,492 B2

CITATION LIST—NON-PATENT LITERATURE

Albertsson, P. A., Partition of Cell Particles and Macromolecules, 1986, John Wiley & Sons, New York.

Björk I., Petersson B. A., Sjöquist J., Some physicocehical properties of protein A from *Staphylococcus aureus*, 1972, Eur. J. Biochem., Vol. 29, pp. 579-584.

Bordier C., Phase separation of Integral Membrane Proteins in Triton X-114 Solution, The Journal of Biological Chemistry, February 1981, Vol. 256, No. 4, pp. 1604-1607.

Johansson H.-O., Karlström G., Tjerneld F., Haynes A. C., Journal of Chromatography B, 1998, Vol. 711, pp. 3-17.

Kula M.-R., Bioseparation, 1990, Vol. 1 pp. 181-189.

McLean M. D., Chen R., Yu D., Mah K.-Z., Teat J., Wang H., Zaplachinski S., Boothe J., Hall J. C., Purification of the therapeutic antibody trastuzumab from genetically modified plants using safflower Protein A-oleosin oilbody technology, Transgenic Research, December 2012, Volume 21, Issue 6, pp 1291-1301.

Terstappen G. C., Geerts A. J., Kula M.-R., The use of detergent based aqoueous two-phase systems for the isolation of extracellular proteins: Purification of a lipase from *Pseudomonas cepacia*, Biotechnol. Appl. Biochem., 1992, Vol. 16, pp. 228-235.

Terstappen G. C., Ramelmeier R. A., Kula M.-R., Protein partitioning in detergent-based aqueous two-phase systems, Journal of Biotechnology, 1993, Vol. 28, pp. 263-275.

Walter H., Brooks D. E. and Fisher D., Partitioning in Aqueous Two-Phase Systems, 1985, Academic Press, Inc., Orlando.

The invention claimed is:

1. A method for purifying proteins with a continuous phase separation technology, wherein the method comprises the steps of:
   a) mixing a surfactant, at least one salt and an aqueous protein solution, which contains at least one hydrophobin, with a further molecule of interest, to form an extraction solution, wherein a part of the extraction solution is transferred to a hear adjustable separation vessel with a first flow speed,
   b) allowing an aqueous phase and a surfactant phase to separate in said separation vessel at an adjustable separation temperature, and
   c) continuously removing a stream of the surfactant phase with a second flow speed, containing at least one hydrophobin with the further molecule of interest, and a steam of the aqueous phase from the extraction solution.

2. The method according to claim 1, wherein the hydrophobin is fused to the further molecule of interest to form a hydrophobin fusion, which is able to carry said molecule of interest into the surfactant phase.

3. The method according to claim 1, wherein the first flow speed and the second flow speed are adjusted together in a way such that the volume of the surfactant phase and the aqueous phase keeps constant in the separation vessel.

4. The method according to claim 1, wherein the surfactant is a non-ionic surfactant.

5. The method according to claim 1, wherein the surfactant is removed and recovered from the surfactant phase, after separation, with an organic solvent in a back extraction process.

6. A method for treating antibody solutions with a phase separation technology, wherein the method comprises the steps of:
   a) mixing at least one hydrophobin, fused to at least one antibody-binding protein, into an aqueous antibody-containing solution to form an aqueous protein solution containing at least one hydrophobin-protein-antibody complex,
   b) adding a surfactant to form an extraction solution,
   c) allowing an aqueous phase and a surfactant phase to separate at a separation temperature,
   d) removing a stream of the separated surfactant phase, containing at least said complex, and a stream of the aqueous phase from the extraction solution, and
   e) adding a low-pH buffer to the separated surfactant phase to release antibody or antibodies from the antibody-binding protein(s) of the formed complex.

7. The method according to claim 6, wherein the antibody-binding protein is originated from a genus *Staphylococcus*.

8. The method according to claim 6, wherein a part of the formed extraction solution from step b) is transferred to a separation vessel with a first flow speed, in which vessel step c) is carried out, followed by carrying out step d) with a second flow speed.

9. The method according to claim 8, wherein the first flow speed is adjusted together with the second flow speed in a way that the volume of the surfactant phase and the aqueous phase keeps constant in the separation vessel during one separation cycle.

10. The method according to claim 6, wherein the hydrophobin-protein fusion, from where antibodies have been released, is recycled back to the step a).

11. The method according to claim 6, wherein a plurality of parallel separation vessels are used.

12. The method according to claim 6, wherein the separation temperature is below 50° C.

13. The method according to claim 6, wherein the surfactant concentration is below 20% of the reaction volume.

* * * * *